US00PP15201P2

(12) United States Plant Patent
McNaughton

(10) Patent No.: US PP15,201 P2
(45) Date of Patent: Oct. 5, 2004

(54) ***SANTOLINA* PLANT NAMED 'SANT101'**

(50) Latin Name: *Santolina pinnata×chamaecyparissus*
Varietal Denomination: Sant101

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,085

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Anne Marie Grunberg
*Assistant Examiner*—June Hwu

(57) ABSTRACT

A new cultivar of *Santolina* named 'Sant101' that is distinguished by prostrate mounding habit, golden-yellow flowers, and grey-green to green finely dissected aromatic foliage. In combination these traits set 'Sant101' apart from all other existing varieties of *Santolina* known to the inventor.

4 Drawing Sheets

Genus: *Santolina.*
Species: *pinnata×chamaecyparissus.*
Denomination: Sant101.

BACKGROUND OF THE INVENTION

The present invention relates to a new and distinct cultivar of lavender cotton, an evergreen sub-shrub that is grown for use as an ornamental landscape plant. The new invention is known botanically as *Santolina×hybrida* and will be referred to hereinafter by the cultivar name 'Sant101'. 'Sant101' will be marketed under the trade name "Shades of Jade". *Santolina* is in the family *Compositae,* under which the commonly referred to "flower" is actually the inflorescence, and made up of smaller ray flowers and disc florets. The ray flowers are what look like "petals". For ease of clarification the common term "flower" is used herein to describe the inflorescence.

'Sant101' is a hybrid plant, bred by the inventor in New Zealand. After being interested in *Santolinas* for twenty years, and attempting to germinate seed without success, the inventor cross-pollinated two *Santolina* plants to produce a new hybrid for commercial use. From the several seedlings that resulted, the inventor selected the new cultivar 'Sant101', for its unique habit and flower color. The selection was made in 1998 in a cultivated area of Christchurch, New Zealand. The female parent plant is an unknown or unnamed plant (possibly not a described cultivar) of the species *Santolina pinnata* subsp. *neapolitana* (unpatented) and the male parent plant is *Santolina chamaecyparissus* 'Lemon Queen' (unpatented). The closest comparison plants are the parent plants. 'Sant101' is distinguishable from *Santolina pinnata* subsp. *neapolitana* by green colored foliage. 'Sant101' is distinguishable from 'Lemon Queen' by larger flowers, that are golden-yellow in color as opposed to the lemon-yellow flowers of 'Lemon Queen'. The prostrate, mounding habit is not typical of the parents, which grow into large rounded bushes.

The distinguishing characteristics of 'Sant101' are prostrate mounding habit and golden-yellow flowers. 'Sant101' also produces large flowers, and delicate cut leaf foliage that exhibits various shades of grey-green to green throughout the summer months. Blooming occurs from mid summer into fall. Cultural requirements include full sun, little or no to moderate water and any well-draining soil. Hardiness is classified as USDA Zone 7.

The first asexual reproduction of 'Sant101' was accomplished by the inventor in 1998 in a cultivated area of Christchurch, New Zealand. The method used was softwood cuttings. Since that time subsequent generations have been determined stable and true to type.

SUMMARY OF THE INVENTION

The following traits have been repeatedly observed and represent the distinguishing characteristics of the new *Santolina* cultivar 'Sant101'. These traits in combination distinguish 'Sant101' from all other existing varieties of *Santolina* known to the inventor. 'Sant101' has not been tested under all possible conditions and phenotypic differences may be observed with variations in environmental, climatic, and cultural conditions, however, without any variance in genotype.

1. *Santolina* 'Sant101' is an evergreen sub-shrub.
2. *Santolina* 'Sant101' exhibits a prostrate mounding habit.
3. *Santolina* 'Sant101' exhibits large bright golden-yellow flowers.
4. The foliage of *Santolina* 'Sant101' is fragrant and exhibits various shades of grey-green to green during the summer months.
5. *Santolina* 'Sant101' exhibits delicate cut leaf foliage.
6. *Santolina* 'Sant101' is 38 cm. in height and 40 cm. in width in a 2-liter container, and 100 cm. in width and 50 cm. in height at maturity.
7. *Santolina* 'Sant101' is used as an ornamental in raised beds, low edgings, rock gardens and herb gardens.
8. *Santolina* 'Sant101' is reproduced asexually using softwood cuttings.
9. *Santolina* 'Sant101' is hardy to USDA Zone 7.

BRIEF DESCRIPTION OF THE DRAWINGS

The accompanying drawings illustrate the overall appearance of the new *Santolina* plant 'Sant101' showing the colors as true as it is reasonably possible to obtain in colored reproductions of this type. Colors in the drawings may differ from the color values cited in the detailed botanical description, which accurately describes the actual colors of the new variety 'Sant101'. The plants were 12–15 months old at the time and planted in the ground from 2-liter containers grown in Arroyo Grande, Calif.

The drawing on sheet 1 shows an entire plant before bloom, and illustrates the neat mounding habit.

The drawing on sheet 2 shows a close-up of the plant, and illustrates the finely dissected gray-green foliage.

The drawing on sheet 3 shows the entire plant in the early stages of bloom. This drawing shows 'Sant101' labeled as "Shades of Jade" which is the designated trade name of 'Sant101'.

The drawing on the sheet 4 illustrates a close-up view of a single flower.

Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Santolina* cultivar 'Sant101'. Observations, measurements, values and comparisons were made in Arroyo Grande Calif. from 12-month-old plants in 2-liter containers and grown out-of-doors. Color determinations are made in accordance with The 2001 Royal Horticultural Society Colour Chart from London England, except where general color terms of ordinary dictionary significance are used. In the Compositae family, under which *Santolina* is classified, the commonly referred to "flower" is actually the inflorescence, and made up of smaller ray flowers and disc florets. For ease of clarification the common term "flower" is used here to designate a category of description. Under this category is the detailed botanical description of the parts of the inflorescence, which is commonly referred to as the "flower" of this plant.

Botanical classification: *Santolina* 'Sant101'.
Species: ×*hybrida*.
Commercial classification: Sub-shrub.
Common name: Lavender cotton.
Parentage: *Santolina* 'Sant101' is a hybrid plant that resulted from the cross hybridization of the following parent plants:
- *Seed parent.*—*Santolina pinnata* subsp. *neapolitana*.
- *Pollen parent.*—*Santolina chamaecyparissus* 'Lemon Queen'.

Propagation method: Softwood cuttings.
Rooting habit: Fine.
Vigor: Vigorous.
Time to develop roots: 2–3 weeks are needed for an initial cutting to develop roots.
Crop time: 9 months are needed to produce a finished 2-liter container from a rooted cutting.
Growth habit: Prostrate mounding habit.
Form: Dense mound.
Suggested container size: 2-liter container.
Use: Ornamental landscape plant for use as a low edging or in herb gardens, rock gardens or raised beds.
Height of plant: 38 cm. in height in a 2-liter container.
Width of plant: 40 cm. in width in a 2-liter container.
Cultural requirements: Grow in full sun with little or no to moderate water and well-drained soil.
Hardiness: USDA Zone 7.
Pest and disease susceptibility: No susceptibility to disease or pest known to the inventor.

Stem:
- *Branching habit.*—Dense basal branching.
- *Stem color.*—191B.
- *Stem dimensions.*—14 cm in length and 3 mm. in width.
- *Stem shape.*—Cylindrical, and with ridges.
- *Stem surface.*—Tomentose.
- *Internode length.*—Length between nodes is 1.25 cm.
- *Fragrance.*—Resinous scent.

Foliage:
- *Type.*—Evergreen.
- *Leaf arrangement.*—Alternate.
- *Leaf division.*—Compound.
- *Leaf shape.*—Finely pinnatisect.
- *Margin.*—Entire.
- *Leaf length.*—2–2.50 cm. in length.
- *Leaf width.*—3 mm. in width.
- *Leaf base.*—Attenuate.
- *Leaf apex.*—Rounded.
- *Leaf venation pattern.*—Pinnate.
- *Vein color* (*abaxial surface*).—191B.
- *Vein color* (*adaxial surface*).—191B.
- *Leaf surface* (*abaxial surface*).—Tomentose.
- *Leaf surface* (*adaxial surface*).—Tomentose.
- *Leaf attachment.*—Petiolate.
- *Petiole dimensions.*—5 mm. in length and 1 mm. in diameter.
- *Petiole shape.*—Cylindrical.
- *Petiole color.*—191B.
- *Durability of foliage to stress.*—High durability.
- *Presence of stipules or spines.*—None.
- *Leaf color* (*adaxial surface*).—The individual colors 191A, 191B, 189A, and 122A are present on individual leaves at individual times throughout the season.
- *Leaf color* (*abaxial surface*).—The individual colors 191A, 191B, 189A, and 122A are present on individual leaves at individual times throughout the season.
- *Fragrance.*—Resinous fragrance.

Flower:
- *Inflorescence.*—Capitate.
- *Type.*—Radiate head.
- *Aspect.*—Facing upward.
- *Dimensions of infloresence* (*radiate head*).—2 cm. in diameter and 1 cm. in height.
- *Inflorescence shape.*—Discoid.
- *Inflorescence color.*—13A.
- *Quantity of inflorescences per plant.*—Approximately 75 to 100.
- *Quantity of flowers per inflorescence.*—Ray florets: Within the range of 60–70 per inflorescence. Disc florets: Within the range of 20–25 per inflorescence.
- *Natural flowering season.*—From mid summer to fall.
- *Peduncle dimensions.*—27 cm in length and 3 mm. in diameter.
- *Peduncle shape.*—Cylindrical and with slight ridges.
- *Peduncle surface.*—Tomentose.
- *Peduncle color.*—191C.
- *Peduncle strength.*—Strong.
- *Bud shape.*—Discoid.
- *Bud dimensions.*—0.75 cm. in height and 1.25 cm. in diameter.
- *Bud color.*—15A.
- *Bud surface.*—Tomentose.

*Self-cleaning or persistent.*—Persistent.
*Ray flower petal surface* (*abaxial surface*).—Glabrous.
*Ray flower petal surface* (*adaxial surface*).—Glabrous.
*Number of ray flower petals.*—Five petals.
*Fused or unfused.*—Petals basally fused.
*Ray flower petal margins.*—Entire.
*Ray flower shape.*—Tubular.
*Depth of corolla tube.*—0.50 mm. in depth.
*Ray flower petal apex.*—Acute.
*Ray flower dimensions.*—5 mm. in length and 0.75 mm. in width.
*Corolla tube color* (*inside*).—15A.
*Corolla tube color* (*outside*).—15A.
*Ray flower petal color* (*adaxial surface*).—15A.
*Ray flower petal color* (*abaxial surface*).—15A.
*Disc floret dimensions.*—5 mm. in length and 0.50 mm. in width.
*Surface of disc floret.*—Glabrous.
*Shape of disc floret.*—Tubular.
*Petals on disc floret.*—Absent.
*Disk floret color* (*apex*).—15A.
*Disk floret color* (*base*).—145A.
*Receptacles* (*bracts on disk florets*).—Absent.
*Number of involucral bracts* (*phyllaries*).—Average of approximately 100 per inflorescence.
*Involucral bract shape.*—Elongated ovate.
*Involucral bract texture.*—Ceraceous texture.
*Involucral bract margin.*—Entire and tomentose.
*Involucral bract apex.*—Acute.
*Involucral bract base.*—Truncate.
*Involucral bract dimensions.*—4 mm. in length and 1 mm. in width.
*Involucral bract color* (*adaxial surface*).—138C.
*Involucral bract color* (*abaxial surface*).—138C.
*Involucral bract surface* (*abaxial surface*).—Lanate.
*Involucral bract surface* (*adaxial surface*).—Glabrous and glossy.
*Fragrance.*—Disagreeable pungent odor.

Reproductive organs:

*Stamens.*—10 stamens per disc floret, that is 200–250 stamens per inflorescence. No stamens have been observed to date in the ray florets.
*Stamen dimensions.*—0.25 mm. in width and 1 mm. in length.
*Stamen shape.*—Distinct filaments adnate to inside of corolla tube.
*Stamen color.*—1D.
*Anther shape.*—Connate.
*Anther color.*—16B.
*Anther dimensions.*—1.50 mm. in length and less than 0.25 mm. in width.
*Quantity of pollen.*—Small amount.
*Pollen color.*—13A.
*Pistil number.*—1 pistil per ray floret; no pistils observed to date in the disc floret.
*Pistil color.*—13A.
*Pistil shape.*—Filament.
*Pistil dimensions.*—5 mm. in length and 0.25 mm. in width.
*Stigma shape.*—Bifid.
*Stigma dimensions.*—Each tip is 1 mm. in length and less than 0.25 mm. in diameter.
*Stigma color.*—13A.
*Style color.*—13A.
*Style dimensions.*—2 mm. in length and 0.25 mm in width.
*Style shape.*—Filament.
*Ovary.*—Inferior.
*Ovary shape.*—Globular.
*Ovary color.*—138D.
*Ovary dimensions.*—0.75 mm. in height and 0.75 mm. in width.

Seed:

*Fruit.*—Color N199B.
*Fruit surface.*—Fleshy or succulent.
*Fruit dimensions.*—1 cm in length×0.5 cm in width.
*Seed length.*—3 mm.
*Seed width.*—1 mm.
*Seed color.*—165C.
*Amount of seed.*—Low, 10% for each inflorescence.

What is claimed is:

1. A new and distinct cultivar of *Santolina* plant named 'Sant101' as described and illustrated.

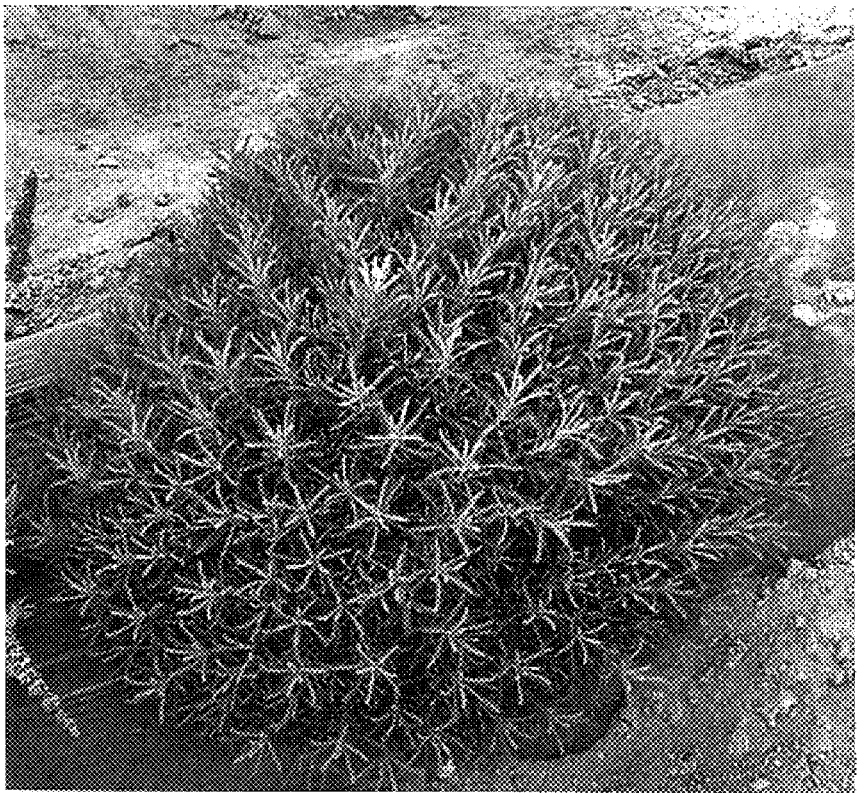

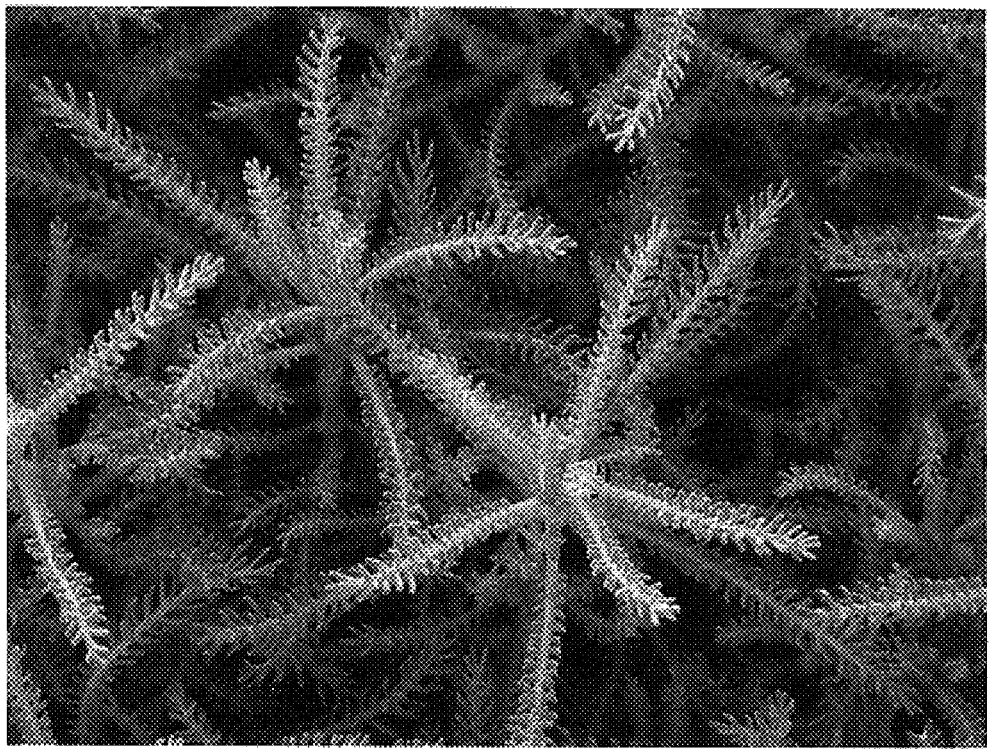

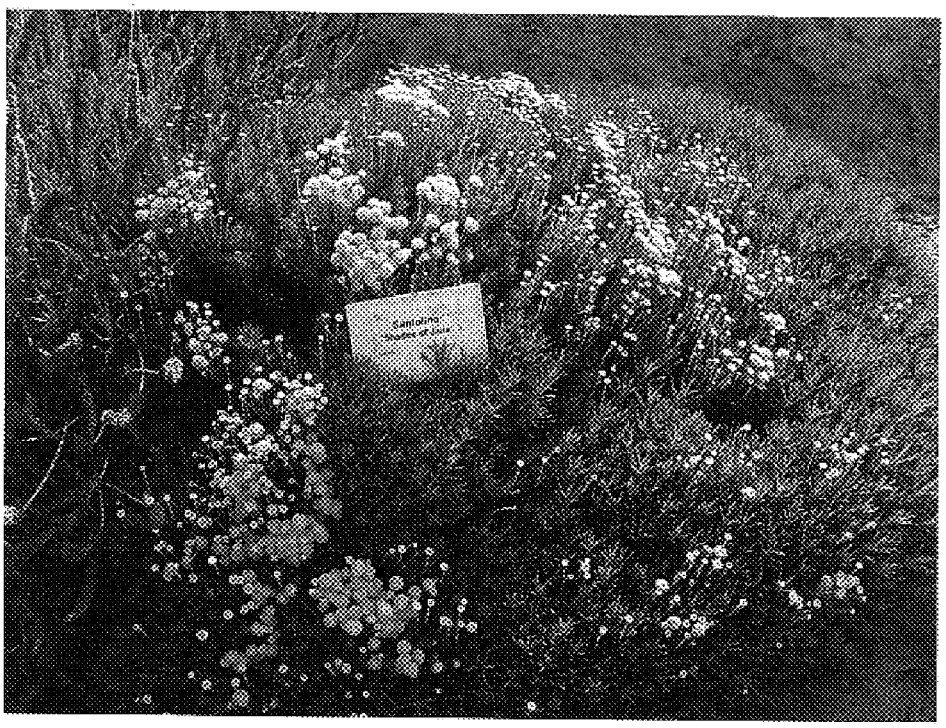

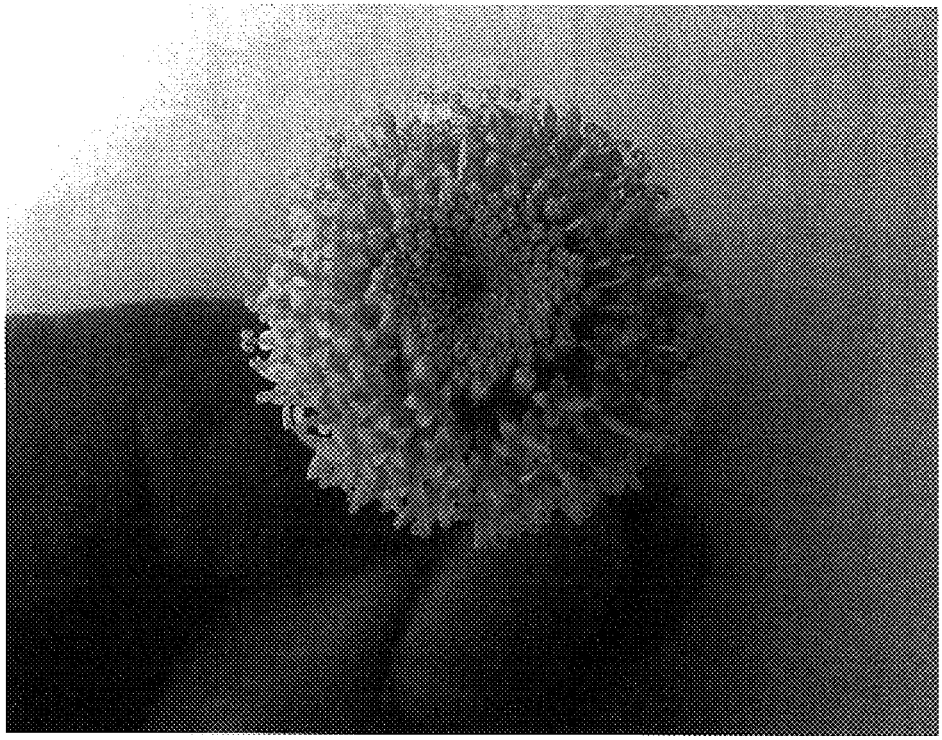

* * * * *